United States Patent [19]

Bisera et al.

[11] 4,409,977

[45] Oct. 18, 1983

[54] HIGH FREQUENCY VENTILLATOR

[75] Inventors: Jose Bisera, Camarillo; Max H. Weil, Beverly Hills, both of Calif.

[73] Assignee: Institute of Critical Care Medicine, Los Angeles, Calif.

[21] Appl. No.: 280,703

[22] Filed: Jul. 6, 1981

[51] Int. Cl.³ .......................................... A61M 16/00
[52] U.S. Cl. ......................... 128/205.15; 128/205.14; 128/204.21; 417/394; 417/478
[58] Field of Search ...................... 128/204.18, 204.21, 128/204.23, 204.24, 204.25, 205.13, 205.14, 205.15, 205.16, 205.17, 205.18, 205.24; 417/394, 478

[56] References Cited

U.S. PATENT DOCUMENTS

| 3,682,166 | 8/1972 | Jacobs | 128/205.24 |
|---|---|---|---|
| 3,964,476 | 6/1976 | Palleni | 128/205.24 |
| 3,993,059 | 11/1976 | Sjostrand | 128/205.24 |
| 4,212,589 | 7/1980 | Bosio | 417/394 |
| 4,215,681 | 8/1980 | Zalkin et al. | 128/205.18 |
| 4,265,237 | 5/1981 | Schwanbom et al. | 128/204.25 |
| 4,270,530 | 6/1981 | Baum et al. | 128/204.25 |

FOREIGN PATENT DOCUMENTS 349022 11/1960 Switzerland ..................... 417/394

OTHER PUBLICATIONS

"Effective Pulmonary Ventilation with Small-Volume Oscillations at High Frequency", *Science*, vol. 209, Aug. 1980.
"High Frequency Percutaneous Transtracheal Jet Ventilation", By-M. Klain, MD. and R. Brian Smith, MD. Critical Care Medicine Copyright, 1977, vol. 5, No. 6.
Smith et al., "Percutaneous Transtracheal Ventilation", JACEP Oct. 1976, vol. 5, No. 10, pp. 765-770.

Primary Examiner—Henry J. Recla
Attorney, Agent, or Firm—Freilich, Hornbaker, Wasserman, Rosen & Fernandez

[57] ABSTRACT

High frequency medical breathing apparatus is provided, which delivers efficiently controlled high frequency air pulses to a catheter, and which is of relatively low cost and is energized by pressured air that is commonly available in a hospital environment. The apparatus includes a large flexible bag with entrance and exit openings, walls forming a sealed chamber around the bag, and a source that applies pressure pulses to the chamber to partially compress the bag at each pulse so as to deliver air through the exit end of the bag and a check valve, and into a catheter that leads to a patient's lungs.

3 Claims, 3 Drawing Figures

HIGH FREQUENCY VENTILLATOR

BACKGROUND OF THE INVENTION

A commonly used technique for ventilating hospital patients, involves the application of low pressure pulses to the airway of a patient, with each pressure pulse causing expansion of the patient's lung to force him to breathe at a typical normal rate such as 16 breaths per minute. This mechanical breathing approach has many disadvantages which are recognized in the field.

A more recently developed technique, commonly referred to as high frequency jet ventillation, involves the application of small volume air pulses (oxygen may be added) to the patient's lung, at a frequency much higher than typical breathing rates, such as above 100 pulses per minute. The air pulses bring oxygen to the alveoli of the lungs without necessitating expansion and contraction of the patient's lungs. While this technique has great promise, the equipment for applying the air pulses has not been highly efficient. One simple approach is to utilize a valve in series with a hospital air supply (typically about 50 psi) and to use an oscillator to turn the valve on and off. Such a high frequency air pulse source is unsatisfactory because of the danger that the valve will stick open, and because it is very difficult to accurately control the volume of air applied to the patient. Another technnique involves the use of a motor driven piston pump which pumps a controlled amount of air at every cycle. However, the air pulses are not of an efficient configuration, and the moving parts of the apparatus increase its cost and maintenance requirements. A high frequency medical breathing apparatus which was of simple construction, which could be easily and safely powered in a hospital environment, and which produced air pulses of high efficiency, would be of considerable value in the furtherance of high frequency ventilation techniques.

SUMMARY OF THE INVENTION

In accordance with one embodiment of the present invention, a high frequency medical breathing system is provided which is relatively simple, safe and efficient. The system can include a compressible container having entrance and exit openings and lying within a pump chamber. Check valves are respectively connected to the entrance and exit openings. A pressure pulse source is provided which cyclically applies pressure pulses to the chamber, to compress the compressible container therein so as to pump breathing gas out of the exit check valve, for application to a patient through a catheter assembly that extends to the patients's lungs. The system can be energized primarily by the use of air from a hospital air supply (e.g. at 50 psi) to supply the pressure pulses to the chamber, and yet prevents the direct application of such high pressures to the patient even in case of valve failure.

The compressible container can be formed of a flexible bag having a much larger volume than the amount of air pumped out of it in each pulse. This permits the bag to apply an air pulse, having a rapid rise and fall, so as to provide maximum patient ventilation with minimal air pumped into the patient.

The novel features of the invention are set forth with particularity in the appended claims. The invention will be best understood from the following description when read in conjunction with the accompanying drawings.

DESCRIPTION OF THE PREFERRED EMBODIMENTS

Figure 1:
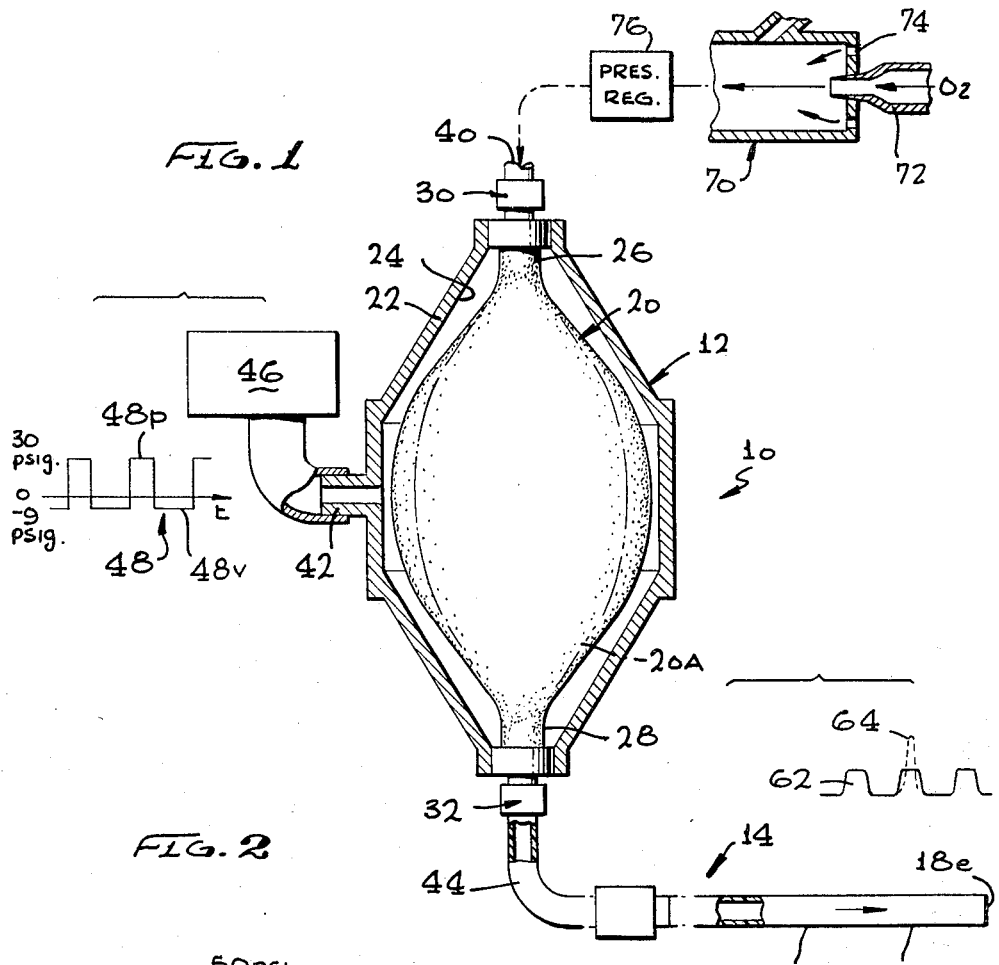
FIG. 1 is a partially sectional elevation view of a high frequency ventilator constructed in accordance with the invention.
Figure 2:
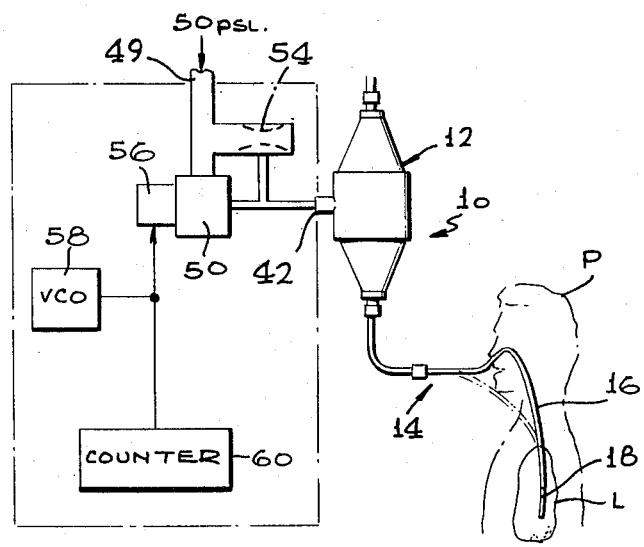
FIG. 2 is an elevation and diagramatic view of the ventilator of FIG. 1.

The figures illustrate a high frequency medical breathing system, or ventilator system 10, which includes an apparatus 12 for applying relatively small volume pulses of air at a relatively high frequency, to a catheter assembly 14 which is introduced into the airway of a patient P (FIG. 2). In systems of this type, the end of the catheter assembly lies in the lung L of the patient. The pulses of fresh air mix with air in the lungs, to bring the fresh air containing higher concentrations of oxygen and lower concentrations of carbon dioxide, to the air sacks of the lungs. Accordingly, ventilation of the patient is accomplished even when the patient's lungs are not repeatedly expanding and contracting. The catheter assembly 14 (FIG. 1) typically includes a catheter 16 of relatively small diameter, such as a 14-gauge catheter with an internal diameter of about 1/16th inch and followed by a 16-gauge needle 18 having about the same inside diameter and having an open end 18e. This relatively small diameter assembly can fit through the airway of the patient without blocking it, so the patient can separately breathe and talk, and there is minimal possibility of inflammation and other harm to the patient. While normal breathing involves the taking of about 15 breaths per minute of about 150 mL (milliliters) per breath, the present apparatus applies air pulses at about ten times that rate, or about 150 pulses per minute at a volume of about 20 mL per pulse, although the frequency and volume per pulse can be varied.

Figure 3:
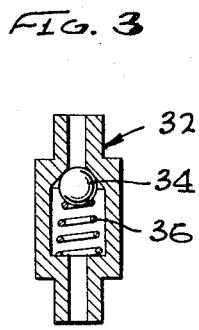
FIG. 3 is a sectional view of a check valve of the ventilator of FIG. 1.

The ventilator apparatus 12 includes a compressible container 20 such as a flexible bag, which lies within a housing 22 forming a pump chamber 24. The bag 20 has entrance and exit ends 26, 28 with openings therein that are connected to check valves 30, 32. Each of the check valves 30, 32 can be of the simple type shown in FIG. 3 which utilizes a ball 34 held against a valve seat by a spring 36 to permit air flow in only a downward direction for the orientation of FIG. 1. The upper check valve 30 has an entrance opening 40 which can be left open to the atmosphere when oxygen is not to be added to the air to be breathed.

The pump chamber 24 has an inlet 42 which receives air pulses that compress the air bag 20, as to the configuration shown at 20A. The compressed air in the bag cannot flow up through the check valve 30, but can flow down through the exit check valve 32 and through a tube 44 into the catheter assembly 14. After each pulse of pressured air, the pressure in the chamber 24 decreases to a low level and the bag 20 can expand again by drawing in air from the atmosphere through the entrance 40 that is open to the atmosphere and through the check valve 30. In order to aid in expansion of the bag 20 to draw in air, the source 46 of pressure pulses, is constructed to apply a vacuum to the chamber 24 between each pressure pulse. The pressure versus time characteristic of the pressure pulse is illustrated by the graph 48, which shows an example wherein pressure pulses of 30 psig (i.e. 30 psi above atmospheric pressure) are followed by negative or vacuum pulses of a level such as −9 psig. The negative pulses assure creation of a pressure difference across the valve 30 to draw in air from the atmosphere into the bag 20, and to draw in such air rapidly.

FIG. 2 illustrates details of the pressure pulse source 46. The apparatus is powered primarily from pressured air, such as at a pressure of 50 psi which is commonly available in a hospital environment. This high pressure is delivered through a tube 49 and through a pressure regulator and valve 50 which is cycled to open and close to deliver pressure pulses of about 30 psig to the pump chamber inlet 42. The compressed air delivered through the tube 48 is also delivered through a venturi device 54, so that a vacuum can be obtained from the throat of the venturi for delivery to the pump inlet 42 when a high pressure pulse is not being delivered thereto. The pneumatic regulator-valve 50 is opened and closed by a solenoid 56 which is operated by a low frequency voltage controlled oscillator 58. The frequency of the oscillator 58 is adjustable to control the rate at which air pulses are delivered to the patient. A simple oscillator 58 can be constructed which is operated by a battery, to avoid the use of the high voltages of wall outlets and the corresponding necessity for safeguards to prevent shocks to patients. A resettable counter 60 is provided to indicate the number of air pressure pulses delivered to a patient during any given time period to aid in monitoring the operation of the equipment.

During operation of the ventillator apparatus 12 (FIG. 1) to deliver air pulses for high frequency ventilation, the bag 20 is compressed by only a small amount of its total volume in each cycle of operation. For example, compression from the state shown at 20 to the state shown at 20A may reduce the volume of a one liter bag by perhaps only 20 mL. Such small compression enables the application of a relatively constant pressure to the catheter system 14 during each pressure pulse. If the percentage of total volume of the bag 20 changed substantially, then there would be a substantial change in the configuration of the bag and the configuration of the space within the pump chamber 24 which lies outside the bag, all of which would affect the pressure delivered to the catheter. By applying apparatus-energizing pressure pulses 48p of relatively rapid rise and fall, together with the use of a relatively large bag, ventilation pressure pulses of relatively rapid rise and fall indicated at 62, are applied from the end of the needle 18e to the patient's lung.

The rise and fall times of the ventilation pulses are lengthened primarily by the restriction of the catheter assembly to the passage of air, and by the length of the catheter which provides a volume in which air accumulates. This is because the air bag 20 has a large volume of more than the average normal breath of about 200 mL, so the cross-sectional area of the catheter of less than one-hundredth square inch is the principal factor limiting the amount of air flow to the patient during the typical bag contraction of less than one second duration.

The air pressure pulses 62 applied to the patient's lung must be fairly energetic to create air currents within the lungs that help to displace the "stale" air in the air sacks that include reduced amounts of oxygen and increased amounts of carbon dioxide, with the fresh air applied through the needle. However, if the air pulses or jets are too energetic, they can do harm by irritating tissue against which they may impact before being reduced in velocity. If air pulses with relatively slow rises and falls were utilized, of the type indicated at 64, then to achieve the same ventilation capacity the peak pressure and velocity of the pulse would have to be increased, resulting in the possibility of more irritation to the patient's airways, as well as more movement of the catheter assembly within the patient due to the reaction of the jet.

In high frequency ventilation, air pressure pulses of perhaps 20 mL are delivered at a frequency of perhaps 150 pulses per minute. In high frequency ventilation the pulses are above 100 pulses per minute. The percentage of each cycle of operation during which a positive pressure at 48p is delivered, as opposed to the vacuum portion at 48v, can be controlled to vary the amount of air delivered in each cycle. Of course, at least a portion of each cycle, such as at least about one-fourth, must be free of the positive pressure pulse to permit bag expansion. This control is in addition to the variation of the frequency of the pulses (which does not greatly vary the amount of air delivered each minute). The ventilator apparatus 12 also can be utilized in the more usual mechanical breathing techniques, wherein low pressure, high volume pulses are delivered at a frequency of perhaps 15 cycles per minute, although in that case a pressure-reducing regulator should be installed at the chamber inlet 42 or some other means must be provided to assure that large pressures are not applied to the patient. The use of a large compressible container or bag 20 therefore facilitates versatile use of the apparatus. The bag 20 can be constructed as a flexible but substantially non-elastic bag, which is able to withstand large pressure differentials, by utilizing a canvas bag whose inside is sealed by a rubber layer.

In many applications, the air delivered to the patient must be enriched by adding oxygen to it. This can be accomplished as by use of a device 70 which includes a jet conduit 72 receiving oxygen and mixing it with air drawn in through openings 74. The enriched air is delivered through a pressure regulator 76 to the air entrance 40, instead of opening the entrance 40 directly to the atmosphere. In one example, the regulator 76 is adjusted to deliver enriched air at a pressure of no more than 5 psi. The exit valve 32 attached to the bag, has a spring precompressed to prevent air passage at less than a 10 psi difference across the valve, to prevent air flow therethrough except when the bag 20 is being compressed. A similar arrangement can be utilized to provide moisturized air. Whether the incoming air is at atmospheric pressure or at the 5 psig level in the preceding example of oxygen-enriched air, the use of a negative pressure 48v between compression of the bag, helps to achieve rapid filling of the bag.

Thus, the invention provides a high frequency medical breathing system that efficiently ventilates a patient by high frequency ventilation techniques, and yet which is of relatively simple and safe construction. This is accomplished by utilizing a compressible container such as a flexible bag, having check valves at its entrance and exit openings and lying within a pump chamber, and by applying pressure pulses to the chamber to cyclically compress the bag. The apparatus for applying pressure pulses to the chamber, can be constructed to apply a vacuum inbetween the pulses, to assure rapid fillup of the bag and permit its efficient utilization even when the input is connected to air at atmospheric pressure. A large compressible container can be utilized, together with a pressure pulse source that compresses the container by only a fraction of its total volume in each cycle of operation, to obtain a controllable pressure pulse from the apparatus. A container having a volume of more than 200 mL, which is more than a typical volume of air injested in each cycle of typical normal breathing by a patient, can be utilized, together with a pressure pulse source that collapses the bag by less than 1/10th its volumetric capacity at full expansion, in each cycle of operation.

Although particular embodiments of the invention have been described and illustrated herein, it is recognized that modifications and variations may readily occur to those skilled in the art and consequently it is intended that the claims be interpreted to cover such modifications and equivalents.

What is claimed is:

1. A high frequency ventillator system comprising:
walls forming a pump chamber with a pair of open ends;
a flexible bag lying in said chamber and having opposite open ends sealed within the open ends of said chamber thereby defining a pressure compartment between said walls and said bag;
entrance and exit check valves connected to said ends of said bag;
a breathing gas source connected to said entrance check valve;
a catheter assembly connected to said exit valve, for applying gas pumped out of said bag into the air passage of a patient; and
a high frequency pressure pulse source connected to said pressure compartment to apply pressure pulses of controlled pressure and duration that compress said bag to pump out gas therefrom;
said bag having a volume great enough that it is compressed less than about one-tenth its volume by each pressure pulse of said source.

2. The system described in claim 1 wherein:
said bag has a volume of at least about 200 millileters, said pressure pulse source is constructed to apply gas pressure on the order of magnitude of 30 psi to said pump chamber for periods of less than one second, and said catheter assembly has a portion with a cross-sectional area of less than one-hundredth square inch.

3. A method for generating ventilation pressure pulses for high frequency ventilation of a patient, comprising:
operating a gas pressure pulse source to apply high frequency gas pressure pulses to the outside of a gas-filled flexible bag to repeatedly compress the bag, connecting the bag to a catheter assembly to apply gas in the bag thereto when pressure is applied around the bag, and connecting the bag to a source of breathing gas and flowing gas from the source to the bag when the bag is not being compressed by the pressure pulses;
said step of applying gas to the catheter assembly includes applying said gas pressure pulses with rapid rises to the outside of said bag and compressing the bag by less than half its volume, with the minimum volume of the bag during its compression being more than 200 milliliters and with the minimum cross-sectional area of the catheter being no more than one-hundredth square inch, so the resistance of the catheter assembly to the flow of gas therethrough limits the amount of air applied to the patient, whereby to obtain a gas pulse to the patient of rapid rise and falloff.

* * * * *